(12) United States Patent
Darkwa et al.

(10) Patent No.: US 7,597,880 B2
(45) Date of Patent: Oct. 6, 2009

(54) MULTIMINERAL NO-MIX RELAXER

(75) Inventors: Adu Gyamfi Darkwa, Olympia Field, IL (US); Eric Osei-Acquah, Lynwood, IL (US); Angela D. Ellington, Flossmoor, IL (US)

(73) Assignee: L'Oreal (FR)

( * ) Notice: Subject to any disclaimer, the term of this patent is extended or adjusted under 35 U.S.C. 154(b) by 635 days.

(21) Appl. No.: 10/372,416

(22) Filed: Feb. 24, 2003

(65) Prior Publication Data

US 2004/0166073 A1  Aug. 26, 2004

(51) Int. Cl.
*A61Q 5/04* (2006.01)

(52) U.S. Cl. ...................... 424/70.2; 132/202
(58) Field of Classification Search ........................ None
See application file for complete search history.

(56) References Cited

U.S. PATENT DOCUMENTS

| 3,288,770 | A | | 11/1966 | Butler |
|---|---|---|---|---|
| 3,412,019 | A | | 11/1968 | Hoover et al. |
| 3,973,574 | A | * | 8/1976 | Minagawa et al. .......... 132/204 |
| 4,237,910 | A | | 12/1980 | Khahil et al. |
| 4,390,033 | A | | 6/1983 | Khalil et al. |
| 4,524,787 | A | | 6/1985 | Khalil et al. |
| 4,772,462 | A | | 9/1988 | Boothe et al. |
| 4,950,485 | A | | 8/1990 | Akhtar et al. |
| 4,992,267 | A | | 2/1991 | DenBiste et al. |
| 5,068,101 | A | | 11/1991 | Akhtar et al. |
| 5,171,565 | A | | 12/1992 | Akhtar et al. |
| 5,275,809 | A | | 1/1994 | Chen et al. |
| 5,376,364 | A | | 12/1994 | Darkwa et al. |
| 5,609,859 | A | | 3/1997 | Cowsar |
| 5,679,327 | A | | 10/1997 | Darkwa et al. |

FOREIGN PATENT DOCUMENTS

GB  1 233 710 A  5/1971

* cited by examiner

*Primary Examiner*—Jyothsna A Venkat
(74) *Attorney, Agent, or Firm*—Lerner, David, Littenberg, Krumholz & Mentlik, LLP

(57) ABSTRACT

The present invention relates to a no-mix hair relaxer formulation and methods of its use. The relaxer includes a synergistic combination of sodium hydroxide and lithium hydroxide and has a pH of between about 12.7 and about 13.2. These no-mix hair relaxers provide excellent hair straightening performance, in 30 minutes or less, with reduced irritation.

10 Claims, No Drawings

MULTIMINERAL NO-MIX RELAXER

BACKGROUND OF THE INVENTION

Hair relaxers generally fall into two categories: mix and no-mix. "Mix" relaxers generally require a two-component system of a cream base and an activator, which are combined prior to use. Darkwa et al., U.S. Pat. No. 5,679,327, which issued Oct. 21, 1997, describes a highly alkaline hair straightening emulsion of this variety. The emulsion described employs a combination of a strong nitrogenous organic base and an alkali metal hydroxide in the presence of an alkaline earth metal cation. While alkaline earth metal hydroxides are characteristically ineffective as permanent hair straighteners or relaxers, the combination with, preferably, lithium hydroxide, is effective for achieving permanent straightening of hair with a treatment time not more than about 30 minutes. So-called "no-mix" relaxers on the other hand are ready to use. They generally are in the form of a liquid, cream, gel, paste or emulsion which can be directly applied to a subject's hair without first, as the term implies, mixing of two or more separate components.

No mix hair relaxers are very convenient and therefore very desirable. However, they suffer from many of the same problems as their mix based counterparts and some which are unique. Some hair relaxers rely on strong organic and/or inorganic bases such as sodium hydroxide (also referred to as lye) to break the disulfide bonds found in hair's structure, thus allowing straightening through the application of mechanical forces. However, in the concentrations used, these strong bases generally exist at a pH of greater than 13.2, a level that is caustic and can be dangerous to unprotected skin if exposed for any great length of time. Even when skin is properly protected and a relaxer is properly formulated, hair relaxers with lye, for example, can become uncomfortable for subjects in as little as about 15 minutes. This can result in premature termination of the treatment, which often affects the degree to which hair can be straightened. And while higher concentrations and higher pH formulations can act more quickly, the amount of discomfort and the length of time that a subject could be exposed to the relaxer vary accordingly. Moreover, lye based products, because of their highly corrosive nature, can be very damaging to the hair, causing breakage and discoloration, as well as the general lack of desirable physical appearance.

Other strong inorganic bases have been used in place of sodium hydroxide. One of the most popular is lithium hydroxide. Lithium hydroxide, at appropriate concentrations, results in a lower pH and therefore is more comfortable and can be applied for longer periods of time. However, lithium hydroxide is not nearly as efficient as sodium hydroxide in obtaining appropriate degrees of hair straightening. The result is the need to expose the subject to a lithium hydroxide based hair relaxer for a longer period of time to achieve similar straightening. This, however, is self defeating. First, subject is drastically inconvenienced as treatment times of greater than 30 minutes are often required. Moreover, although more comfortable in the short term, upon longer exposure times necessary to obtain appropriate straightening, subjects often complain of scalp discomfort and burning sensations before the ideal treatment time has elapsed. Interrupting treatment at that point yields suboptimal results.

Still another problem is that the natural color or tint of the user's hair can be altered. For example, if the user's hair is initially naturally gray in color, treatment can result in a visible yellowing of the hair. Such discoloration is undesirable. For example, a yellow tinge on gray hair is particularly undesirable because the white fibers in gray hair normally have a desirable natural bright tone which gives the hair highlights, whereas, when yellowed, this same hair looks dull, drab and lacks luster.

Permanent hair straightening should be achieved as quickly as possible to minimize skin irritation, hair damage, and/or hair discoloration from exposure to alkali. For persons having a "fine" type of hair, this can be generally readily achieved. However, for persons having "normal" and especially "coarse to resistant" hair, generally longer treatment (contact) times or greater concentrations of alkaline material or both are needed to effect permanent hair straightening. It is generally recognized in the hair straightening art that prolonged exposure (contact) of hair to the highly alkaline conditions required for permanent hair straightening increases the possibilities of irritating the scalp and hair line skin, of weakening the strength of the treated hair, and of hair discoloration. Thus, even though the extent of permanent hair straightening tends to improve in direct proportion to increased alkalinity and treatment (contact) time, so does the advent or likelihood of these adverse, undesired problems. To avoid or minimize such problems, it is common to limit the treatment time (that is, the time of contact between the emulsion and the user's scalp and hair) to a period that is not longer than about 30 minutes as is known to those familiar with the art.

In addition to these concerns, no-mix formulations must be storage stable and ready to go at a moment's notice. However, oxygen and/or moisture can seep into packaging, which can react with the hydroxide species, reducing potency and efficacy. Providing completely moisture proof packaging is possible. However, that would be very expensive. Therefore, something needs to be done to protect no-mix relaxers and to ensure potency and efficacy at time of use.

Add to these problems the significant problems of ensuring that the product has the right consistency, is easy to apply and remove, is pleasant to work with for stylists who use it time and time again, day in and day out, and for clients as well. One can readily appreciate the difficulties in obtaining a safe, reliable, cost effective and desirable product.

Perhaps because of their respective associated highly alkaline pH (the usual range being as above-indicated), either one of such prior art types of permanent hair straightening emulsions can cause problems. One problem is that skin irritation can result, particularly when the prior art hair straightening emulsion is allowed to remain in contact with the user's hair or skin for more than an acceptable time period. Another problem is that the user's hair can become structurally weakened during treatment so that excessive hair breakage in the resulting straightened hair results.

There remains a substantial and long felt need for improved formulations which employ relatively lower pH levels and which can achieve substantially complete permanent hair straightening of naturally curly, previously untreated, and even coarse hair within a hair contact time period of not more than about 30 minutes. Preferably such improved formulations also demonstrate reduced skin irritation and are both easy and economical to produce and use. The present invention provides such formulations.

SUMMARY OF THE INVENTION

This invention relates to a new and improved formulation for permanently straightening hair, including previously untreated naturally curly hair on the scalp of a user through direct contact of the formulation with the hair. Emulsions of two or more phases are preferred; however, solutions, suspensions, dispersions, gels, creams and lotions may be formulated.

The multimineral no-mix hair relaxer of the present invention accomplishes what other products have promised but have been unable to deliver. Specifically, by providing a no-mix hair relaxer with carefully controlled and effective amounts of both sodium hydroxide and/or potassium and lithium hydroxide, a desirable degree of hair straightening can be obtained in less than 30 minutes, preferably less than about 25 minutes, using a formulation whose pH is about 13.2 or less. This provides the comfort, convenience and performance desired by stylists and their clients alike.

One of the important subjectively evaluated attributes used to judge hair relaxers is irritation. Another is the natural color of the hair and the brightness of its tone. Discoloration or changes in hair color following an alkali-straightening procedure can be undesirable. For example, dark hair, especially dark brown and black hair, can become reddened, faded or dulled. Particularly troublesome is yellowing of natural white (gray) hair. Another important attribute that can be subjectively seen is an undesirable delustering of the natural sheen or luster associated with the previously described discoloration of the natural color of the hair.

One of the benefits of using the improved hair straightener formulations of this invention is good hair condition and non-yellowing or substantial non-discoloration of treated hair. The synergistic action of the hydroxide species used in specified amounts provides rapid action at lower pH and with shorter exposure times, providing reduced irritation.

The multimineral, no-mix hair relaxer formulations of the present invention generally include no more than about 54% NaOH relative to the total amount of NaOH and LiOH in the formulation. More preferably, however, the amount of NaOH is 50% or less. Conversely, while the amount of LiOH in the formulation, as a percent of the total of NaOH and LiOH can be as low as about 46%, it is preferably present in an amount of at least 50% and more preferably greater than 50% based on the total amount of NaOH and LiOH. Potassium hydroxide may be used in place of some or all of the NaOH.

In one aspect of the present invention, there is provided a no-mix multimineral hair relaxer formulation that includes amounts of sodium hydroxide (NaOH) and/or potassium hydroxide (KOH) as well as lithium hydroxide (LiOH) effective to permanently substantially straighten hair in about 30 minutes or under with a minimum of skin irritation, damage or discoloration to the hair.

In one aspect of the present invention, there is provided a no-mix hair relaxer formulation including an effective amount of at least one first hydroxide which is LiOH and at least one second hydroxide selected from the group consisting of NaOH and KOH, and mixtures thereof. These hydroxides are mixed with at least one cosmetically acceptable additive. The formulation has a pH of between about 12.7 and about 13.2.

Stated another way, there is provided a no-mix multimineral hair relaxer formulation that includes effective amounts of NaOH and LiOH and which have a pH of between about 12.7 and about 13.2. More preferably, this formulation is, when properly used, capable of permanently substantially straightening hair in about 30 minutes or under with a minimum of skin irritation, damage or discoloration to the hair. The formulation generally includes not only LiOH and at least one of NaOH and KOH, but a cosmetically acceptable additive. Even more preferably, the formulations in accordance with this aspect of the present invention will have a pH of between about 12.7 and about 13.16. Most preferably, the formulations in accordance with this aspect of the present invention will have a pH of between about 12.7 and about 13.0. These pH ranges are based not only upon the amount of NaOH and/or KOH and LiOH in the formulation, but the contribution of other ingredients as well. As discussed herein, the formulations of the present invention can also include, inter alia, certain oxygen stabilizers such as calcium hydroxide. When present, calcium hydroxide would influence the actual pH of the formulation higher. For example, a formulation including a 50/50 mixture of solutions of NaOH (concentration 0.56 milliequivalents/gram (meq/g)) and LiOH (concentration 0.62 meq/g) produces a pH at 25° C. of about 13.05. However, a formulation in accordance with this invention including a 50/50 mixture of NaOH and LiOH as described in Table 1 would have a pH of about 13.16. What is important is that the formulations of the invention include the specified amounts of NaOH and/or KOH and LiOH and that the final formulation have a pH of between about 13.2 and about 12.7, ±0.05 pH units. NaOH is preferred. Accordingly, in a preferred aspect of the present invention, there is provided a no-mix hair relaxer formulation including LiOH in an amount of between about 0.74% and about 1.53% by weight, and NaOH provided in an amount of between about 0.11% and about 1.23% by weight. The hydroxides are mixed within at least one cosmetically acceptable additive. The formulation has a pH of between about 12.7 and about 13.2.

In another aspect of the present invention, there is provided a no-mix multimineral hair relaxer formulation that includes between about 5 and about 54% sodium hydroxide (NaOH) and between about 46 and about 95% lithium hydroxide (LiOH). These percentages are based on the total amount of NaOH and LiOH in the formulation. More preferably, this formulation is, when properly used, capable of permanently substantially straightening hair in about 30 minutes or under with a minimum of skin irritation, damage or discoloration to the hair. Formulations in accordance with this aspect of the present invention preferably have between about 5% and about 50% NaOH and between about 50% and about 95% LiOH. Even more preferably, the maximum amount of NaOH is about 50% and the minimum amount of LiOH is about 50%. Most preferably, the amount of NaOH in the formulation is less than the amount of LiOH. Where potassium hydroxide is used in place of some or all of the NaOH, it can be substituted 1 for 1 on an active hydroxide basis, so long as the pH of the formulation remains within the desired range of 12.7-13.2.

In another aspect of the present invention, there is provided a no-mix multimineral hair relaxer formulation that includes between about 0.56 and about 0.75 milliequivalents per gram of total NaOH and LiOH.

In another aspect of the present invention, there is provided a no-mix multimineral hair relaxer formulation that includes between about 5 and about 54% sodium hydroxide (NaOH) and between about 46 and about 95% lithium hydroxide and the formulation has a pH of between about 12.7 and about 13.2 and can, when properly used, permanently substantially straighten hair in about 30 minutes or under with a minimum of skin irritation, damage or discoloration to the hair.

In a more preferred aspect of the present invention, there is provided a no-mix multimineral hair relaxer formulation that includes between about 5 and about 50% sodium hydroxide (NaOH) and between about 50 and about 95% lithium hydroxide and the formulation has a pH of between about 12.7 and about 13.16 and can, when properly used, permanently substantially straighten hair in about 30 minutes or under with a minimum of skin irritation, damage or discoloration to the hair.

KOH can be used instead of NaOH in any of these formulations. However, the pH of the resulting formulations should not change. Therefore, if some or all of the NaOH is replaced with KOH, the amount used must be sufficient, in combination with the corresponding amount of LiOH used, to produce the same pH. NaOH is, however, preferred over KOH or mixtures of KOH and NaOH.

In another aspect of the present invention, there is provided a stabilized formulation by providing as a cosmetically acceptable additive a oxygen scavenger such as, preferably, calcium hydroxide. The presence of calcium hydroxide or other suitable oxygen scavenger helps maintain the efficacy and potency of the formulation, even when exposed to low level moisture over prolonged storage periods.

The hair straightening formulations of this invention also preferably include cosmetically acceptable carriers and/or cosmetically acceptable additives such as water or other solvents, lipophilic oleaginous material, and emulsifiers both generally being as known to the prior art. This incorporation is desirable because it enables use of conventional formulating and manufacturing techniques.

The hair straightening products of this invention are particularly effective when they contain certain types of hair conditioners as additives. Particularly preferred hair conditioners for incorporation into such preferred products are the non-polymeric long chain quaternary ammonium compounds which are classified as behenyltrimonium salts, such as behenyl trimethyl ammonium methosulfate, referred to for convenience as BTMS, and behenyl trimethyl ammonium chloride, referred to for convenience as BTMC. Also preferred as hair conditioners are quaternary nitrogen-containing polymers which are homopolymers, copolymers and terpolymers having a polydimethyldiallylammonium chloride (DMDAAC) moiety. Particularly preferred are the homopolymer of polydimethyldiallylammonium chloride (polyDMADAAC) and copolymers thereof containing DMDAAC groups and the polyDMDAAC that is commonly known as POLYQUATERNIUM-6.

The hair straightening formulations of this invention are no more weakening to the user's hair than prior art hair straighteners that are more highly alkaline. Also, the inventive products are effective permanent hair straighteners yet they are substantially non-yellowing to natural gray hair. Additionally, unlike conventional no-lye type hair straightener products, the hair straighteners of this invention particularly do not develop on standing an objectionable odor of ammonia (as the nitrogenous base undergoes its characteristic degradation).

The present invention also provides new and useful methods of making new and improved hair straightening formulations as well as new and useful methods of using new and improved hair straightening formulations. These methods include a method of straightening hair on the head of a subject. First, a hair relaxer formulation including an effective amount of at least one first hydroxide which is LiOH and at least one second hydroxide selected from the group consisting of NaOH and KOH, and mixtures thereof, said hydroxides mixed with at least one cosmetically acceptable additive, the formulation having a pH of between about 12.7 and about 13.2 is provided. Then it is applied to the hair of the subject for a period of not more than 30 minutes.

DETAILED DESCRIPTION

This invention relates to new and improved formulations or products for permanently straightening hair, including previously untreated naturally curly hair. These formulations can exist in many forms such as, without limitation, creams, pastes, liquids, gels and emulsions. Emulsions (two or more phases) are preferred and the formulations or products of the invention will often be described as being emulsions. That should not be considered a limitation on the form of the formulation except where the context suggest otherwise.

The multimineral no-mix hair relaxers of the present invention accomplishes what other products have promised but have been unable to deliver. Specifically, by providing a no-mix hair relaxer with carefully controlled amounts of both sodium hydroxide (and/or potassium hydroxide) and lithium hydroxide, a desirable degree of hair straightening can be obtained in less than 30 minutes, preferably less than about 25 minutes, using a formulation whose pH is about 13.2 or less. This provides the comfort, convenience and performance desired by stylists and their clients alike.

In one aspect of the present invention, there is provided a no-mix multimineral hair relaxer formulation that includes effective amounts of both NaOH and LiOH to permanently substantially straighten hair in about 30 minutes or under with a minimum of skin irritation, damage or discoloration to the hair. Some or all of the NaOH can be replaced with KOH.

The no-mix multimineral hair relaxer formulations of the present invention generally include effective amounts of both NaOH and/or KOH and LiOH. The finished formulations will also possess a pH of between about 12.7 and about 13.2. Even more preferably, the formulations in accordance with this aspect of the present invention will have a pH of between about 12.7 and about 13.16. Most preferably, preferably, the formulations in accordance with this aspect of the present invention will have a pH of between about 12.7 and about 13.0.

The no-mix multimineral hair relaxer formulations of the present invention generally include between about 5 and about 54% NaOH and between about 46 and 95% LiOH. These percentages are based on the total amount of NaOH and LiOH in the formulation. When KOH is used in place of some or all of the NaOH, a proportional amount is used as long as the finished formulation has a pH between about 12.7 and about 13.2. That is the amount of KOH used provides an equivalent amount of active hydroxide as would be provided by a specified amount of NaOH, which may slightly alter the relative weights of LiOH, NaOH and KOH used in the formulation. Preferably, these formulations have between about 5% and about 50% NaOH and between about 50% and about 95% LiOH. Even more preferably, the maximum amount of NaOH is about 50% and the minimum amount of LiOH is about 50%. Most preferably, the amount of NaOH in the formulation is less than the amount of LiOH.

When stated in terms of the number of milliequivalents per gram, the total content of NaOH and LiOH ranges from about 0.56 to about 0.75.

The total amount of NaOH, again on a weight/weight basis based on the weight of the dry anhydrous alkali hydroxide, ranges from between about 0.11 and about 1.23% by weight of the total formulation. More preferably, the amount of NaOH will range from between about 0.11 and about 1.14% and even more preferably, between about 0.11 and about 0.57% by weight of the formulation. An equivalent amount of KOH may be used in place of some or all of the NaOH. The total amount of LiOH, also on a weight/weight basis based on the weight of the dry anhydrous alkali hydroxide, ranges from between about 0.74 and about 1.53% by weight of the total formulation. More preferably, the amount of LiOH will range from between about 0.81 and about 1.53% and even more preferably, between about 1.21 and about 1.53% by weight of the formulation. These weight percents will change if some or all of the NaOH is changed to KOH.

Table 1 below demonstrates changes in pH with varying relative proportions of NaOH and LiOH.

TABLE 1

| | Composition % | | | | | | | | |
|---|---|---|---|---|---|---|---|---|---|
| NaOH relaxer | 100 | 75 | 54 | 50 | 25 | 15 | 10 | 5 | 0 |
| LiOH relaxer | 0 | 25 | 46 | 50 | 75 | 85 | 90 | 95 | 100 |
| pH mix | 13.6 | 13.36 | 13.2 | 13.16 | 13.0 | 12.87 | 12.81 | 12.77 | 12.7 |
| % NaOH (wt) (dry) | 2.28 | 1.71 | 1.23 | 1.14 | 0.57 | 0.34 | 0.23 | 0.11 | 0.00 |
| % LiOH x $H_2O$ (wt) | 0.00 | 0.71 | 1.30 | 1.42 | 2.12 | 2.41 | 2.55 | 2.69 | 2.83 |
| % LiOH (wt) (dry) | 0.00 | 0.40 | 0.74 | 0.81 | 1.21 | 1.37 | 1.45 | 1.53 | 1.61 |

As notable from the table, a composition containing 75% NaOH (1.71 wt % NaOH/0.40 wt % LiOH) yields a pH of 13.36. Relaxers with pHs in this range, generally higher than 13.2, tend to be irritating and can result in hair damage and discoloration. On the other hand, a formulation which is 100% LiOH, having a pH of about 12.7, will often take too long to yield acceptable results in terms of hair straightening, particularly for clients with regular and coarse hair.

In a preferred embodiment, initially present in a product of this invention is an oxygen scavenger that is preferably an alkaline earth metal oxide or hydroxide and most preferably calcium hydroxide. As above-indicated, calcium hydroxide is generally ineffective as a permanent hair straightener when used by itself as the sole strong chemical base in an emulsion. The amount of scavenger present in the formulation can vary with the number of factors including the type of packaging, how long the product will likely sit on a shelf before use, the particle scavenger selected, etc. However, generally the amount of calcium hydroxide included ranges from between about 0.30 to about 0.50 weight percent based on the total formulation. In the case of $Ca(OH)_2$, more can be used, but it may provide a dull look to the hair. Other scavengers can be provided in an amount that provides oxygen scavenging equivalent to the stated amount of calcium hydroxide. If $Ca(OH)_2$ or other base is present, it may influence the overall pH of the formulation. However, when discussing the pH of the formulation, unless otherwise indicated, pH is described as a function of the entire formulation not just the NaOH/KOH/LiOH.

The hair relaxer formulations of the present invention produce a substantially complete permanent straightening of the user's initially naturally curly hair when in contact therewith for a time period that is not longer than about 30 minutes, preferably less than about 25 minutes and more preferably less than about 20 minutes. The user's hair can be classified as fine, normal or coarse to resistant. These hair relaxers are also substantially nonirritating to a user's scalp and hairline skin during the contact time of not more than about 30 minutes. As noted above, the amount of scavenger reported is the amount initially provided. However, because the scavenger may change its chemical form when it reacts with oxygen or moisture, the amount present at a given time after formulation could decrease. Indeed, if left long enough in a moist environment, the amount could have been reduced to zero. However, in the case of calcium hydroxide, the presence or absence of this material should be confirmable based on the presence of residual calcium found in the formulation. Preferably a hair straightening products of this invention has a shelf-life chemical stability of at least about one hour and preferably at least about one month. Even more preferably, the products of the invention have a shelf life of at least about three months and even more preferably, one year.

Preferably present in formulations of the invention are both a lipophilic oleaginous material (preferably emulsified in an oil phase of an emulsified formulation), and when an emulsion is desired, at least one emulsifier that is preferably a lipophilic emulsifier, hydrophilic emulsifier or mixture thereof.

Preferably in an emulsion form of the invention on a 100 weight percent total emulsion product basis the quantity of lipophilic oleaginous material is in the range of about 5 to about 60 weight percent, the quantity of emulsifier is in the range of about 0.01 to about 25 weight percent, and the quantity of the water is in the range of about 35 to about 50 weight percent.

Preferably in an emulsion form of the hair relaxer products of the invention, the lipophilic oleaginous material is selected from the group consisting of petrolatum, mineral oil, mineral jelly, lanolin, waxes, water-insoluble silicones, and mixtures thereof.

Preferably the emulsifier, if used, comprises on a 100 weight percent total emulsion basis:
(a) about 2 to about 20 weight percent of a lipophilic nonionic emulsifier, and
(b) about 0.01 to about 10 weight percent of a hydrophilic emulsifier.

Preferably in such an emulsifier system, the lipophilic nonionic emulsifier is a fatty alcohol derived from fatty acids containing about 12 to about 24 carbon atoms and adducts of said fatty alcohols with alkylene oxides containing at least two and less than four carbon atoms per starting alkylene oxide molecule, and mixtures thereof.

Also, preferably in such an emulsifier system, the hydrophilic emulsifier is selected from the group consisting of amphoteric surfactants, zwitterionic surfactants, nonionic surfactants, anionic surfactants and mixtures thereof.

Optionally, but preferably, an emulsion form of the hair relaxer products of this invention contains an effective hair conditioning amount of hair conditioner. Preferably such a hair conditioner can be selected from the group consisting of water-dispersible monomeric quaternary ammonium compounds containing a long chain aliphatic group having from about 20 to about 24 carbon atoms inclusive and salts thereof, quaternary nitrogen containing polymers and salts thereof, and mixtures thereof. Preferably also, such a hair conditioner is selected from the group consisting of behenyl trimethylammonium methosulfate, behenyl trimethylammonium chloride, and mixtures thereof.

It has now been surprisingly found that substantially complete permanent hair straightening, also referred to herein as "permanently substantially straightening hair," can be achieved with the substantially decreased amounts of combined strong chemical bases that are here employed, compared to prior art formulations wherein these same bases are separately employed in operable amounts. The present emulsion products surprisingly employ respective amounts of strong chemical bases that are ineffective by themselves for hair straightening.

Briefly described, a no-mix emulsion style hair relaxer formulation of this invention can include, on a 100 weight percent basis, about 5% to about 65 weight percent of lipophilic oleaginous material; about 0.01 to about 25 weight percent of lipophilic emulsifier, hydrophilic emulsifier and mixtures thereof and the balance being water.

More particularly, such hair relaxer formulations of this invention comprise on a 100 weight percent basis:
(a) about 15 to about 40 weight percent of a lipophilic oleaginous material;
(b) about 3 to about 15 weight percent of a lipophilic nonionic emulsifier;
(c) about 0.01 to about 10 weight percent of a hydrophilic emulsifier;
(d) about 0.1 to about 10 weight percent of an aliphatic polyhydroxy compound which is liquid at room temperature;
(e) about 0.3 to about 0.5 weight percent of calcium hydroxide (weight based on dry, anhydrous hydroxide);
(f) about 0.74 to about 1.53 weight percent of lithium hydroxide and about 0.11 to about 1.23% by weight of sodium hydroxide (weight based on dry, anhydrous hydroxide), the exact minimum amount used in this range being sufficient to produce a pH of between 12.7 and 13.2; and
(g) about 40 to about 45 weight percent water.

In one preferred conditioning hair straightening emulsion embodiment, the emulsion additionally includes, on a 100 weight percent basis, about 0.01 to about 5 weight percent of at least one hair conditioning agent that is a water dispersible quaternary nitrogen containing polymer, a monomeric quaternary ammonium compound containing a long chain aliphatic group having from about 20 to about 24 carbon atoms inclusive and combinations thereof.

The term "hair conditioning agent" or "hair conditioner" as used herein are synonymous and refer to substantially water-soluble quaternary nitrogen containing compounds which under certain circumstances are substantive to hair.

Lithium hydroxide is commercially supplied as free-flowing crystals of lithium hydroxide monohydrate, assayed as about 57.2% lithium hydroxide. For convenience, references made herein to the term "lithium hydroxide" denote the monohydrate form as supplied. However, when discussing the amounts of lithium hydroxide used, the anhydrous form is contemplated. References made to "weight percent" of lithium hydroxide, therefore, are expressed as lithium hydroxide alone. NaOH can come in a powder or a 50/50 aqueous solution. The solution is preferred. However, weights and weight percentages reported herein are based on dry anhydrous NaOH unless specified otherwise. Weights for KOH and Ca(OH)$_2$ are also based on dry anhydrous materials.

The choice of hair conditioning agent is believed to be limited only by its solubility and its ability to effect conditioning during the chemical relaxation step of the process or to produce a substantive conditioned effect on the relaxed hair, so long as it does not interfere with the action of the active hair relaxing agent.

A preferred water soluble hair conditioning agent is a cationic quaternary ammonium compound which is substantive to the hair and retains a cationic positive charge at a pH above at least 12. Preferably, the hair conditioning agent is present in an emulsion product in an amount of about 0.01 to about 5 weight percent, more preferably about 0.05 to about 1.5 weight percent, and most preferably about 0.1 to about 1 weight percent, calculated on a dry solids basis of the total weight of the hair straightener composition.

Cationic conditioning compounds include any number of quaternary nitrogen containing polymeric and non-polymeric materials well known in the art. For example, cationic compounds include monomeric quaternary ammonium salts, quaternary nitrogen containing polymers and aminofunctional silicone polymers having a polar amine group which develops a net positive charge in an aqueous solution. Monomeric quaternary ammonium compounds containing an aliphatic group from about 20 to about 24 carbon atoms are preferred. Quaternary nitrogen containing polymers are preferred, and, in particular, those which can also modify viscosity as thickeners. The term "quaternary nitrogen containing polymer" as used herein denotes polymers having at least one available quaternary nitrogen atom per molecule.

A number of quaternary nitrogen-containing compounds, their manufacturers and general descriptions of their chemical characteristics can be found in the CTFA Dictionary and in the International Cosmetic Ingredient Dictionary, Vol. 1 and 2, 5th Ed., published by the Cosmetic Toiletry and Fragrance Association, Inc. (CTFA) (1993), the pertinent disclosures of which are incorporated herein by reference. The name assigned to the ingredients by the CTFA or by the manufacturer is used for convenience.

Particularly preferred are the non-polymeric long-chain length ($C_{22}$) quaternary ammonium compounds which are behenyltrimonium salts, such as behenyl trimethyl ammonium methosulfate (BTMS) identified by the CTFA name, BEHENTRIMONIUM METHOSULFATE and N,N,N-trimethyl-1-docosanaminium chloride (BTMC) identified by the CTFA name, BEHENTRIMONIUM CHLORIDE. These materials are sold commercially under the trademarks INCROQUAT BEHENYL® TMS and INCROQUAT® BEHENYL TMC by Croda Inc., New York, and VARISOFT by Witco Corp., New York.

BTMS and BTMC are commercially supplied as wax suspensions or solutions in cetearyl alcohol at an active quaternary concentration of about 24-26%. References to weight percent BTMS or to BTMC, therefore, refer to the material as supplied and reference to active weight percent refers to weight percent based on active quaternary concentration. An active quaternary weight percent concentration of about 0.5 to about 4 weight percent, preferably from about 0.75 to about 2.0 weight percent, and most preferably of about 1 to about 1.0-2.0 weight percent can be used for achieving conditioning benefits. The upper amount of behenyltrimonium compound generally is not limited other than by cost considerations.

Quaternized nitrogen-containing organic polymers which are particularly preferred for achieving substantive hair conditioning benefits are quaternary nitrogen-containing polymers prepared by the polymerization of a diallylamine, preferably dialkyldiallylammonium salt or copolymer thereof in which the alkyl group contains 1 to about 18 carbon atoms, and more preferably where the alkyl group is methyl or ethyl; copolymers containing a cationic component derived from the monomer of dialkyldiallylammonium salt and an anionic component derived from anionic monomers of acrylic acid and methacrylic acid, and polyampholyte terpolymers thereof having as the cationic component, a monomer which is a derivative of diallylamine, preferably a dimethyldiallylammonium salt, an anionic component derived from anionic monomers of acrylic acid or 2-acrylamido-2-methylpropane sulfonic acid and a nonionic component derived from nonionic monomers of acrylamide. Details concerning the preparation of such quaternary nitrogen containing polymers can be found, for example, in U.S. Pat. Nos. 3,288,770; 3,412,019; 4,772,462 and 5,275,809, the pertinent disclosures of which are incorporated herein by reference.

Particularly preferred are the chloride salts of the foregoing quaternized homopolymers and copolymers in which the alkyl group is methyl or ethyl, which are available in a range of weight average molecular weights as aqueous compositions containing about 40 percent polymer solids sold under the trademark MERQUAT® by Ondeo/Nalco Naperville, Ill. 60563-1198.

For example, the homopolymer, dimethyldiallyl ammonium chloride (polyDMDAAC) has the CTFA name, POLYQUATERNIUM-6, is described as having a weight average molecular weight of approximately 100,000 and is sold under the trademarks MERQUAT®-100 by Ondeo/Nalco and ALCOFIX® 131 by Allied Colloids Inc., Suffolk, Va. It is well known that substantive conditioning effects can be produced when POLYQUATERNIUM-6, is present as an ingredient in a no-base, alkali hair straightener. Such products have been patented and commercialized by the assignee of this invention. However, it has now surprisingly been found that about half of the amount of POLYQUATERNIUM-6 normally used in a no-lye hair straightener can produce substantially equivalent substantive conditioning effects when it is used in combination with the non-polymeric conditioner, BTMS, in the no-lye straightener products of this invention.

Other useful copolymers include a copolymer reaction product of DMDAAC with acrylamide monomers having the CTFA name, POLYQUATERNIUM-7, which is described has having a weight average molecular weight of approximately 500,000 and is sold under the trademark MERQUAT®-550. Another copolymer is the reaction product comprised of 80 percent by weight DMDAAC and 20 percent by weight of an anionic monomer of acrylic acid, has the CTFA name, POLYQUATERNIUM-22, is described as having a weight average molecular weight of about 1,300,000 and is sold under the trademark MERQUAT®-280. Details for the preparation of POLYQUATERNIUM-22 and its related polymers is described in U.S. Pat. No. 4,772,462 issued to Boothe et al., the pertinent disclosures of which are incorporated herein by reference.

Also useful is an ampholyte terpolymer comprised of a nonionic component derived from the monomer acrylamide (AM), a cationic component derived from the cationic monomer dimethyldiallylammonium chloride (DMDAAC), and an anionic component derived from the anionic monomer of acrylic acid (AA) or 2-acrylamido-2-methylpropane sulfonic acid (AMPSA) or combinations of AA and AMPSA, described as having a weight average molecular weight of from about 10,000 to about 10 million. An exemplary terpolymer is sold under the trademark MERQUAT® PLUS in varying viscosity grades, identified by the CTFA name POLYQUATERNIUM-39. Details for the preparation of such terpolymers is described in U.S. Pat. No. 5,275,809 issued to Chen et al., the pertinent disclosures of which are incorporated herein by reference. POLYQUATERNIUM-6 is particularly preferred.

Other useful polymeric quaternary ammonium salts are the homopolymer and the 2-propenamide polymer of ethanaminium, which is structurally identified as N,N,N-trimethyl-2-[(2-methyl-1-oxo-2-propenyl)Oxylchloride and which are respectively identified by the CTFA names, POLYQUATERNIUM-37 and POLYQUATERNIUM-32, are sold under the trademarks SALCARE® SC95 and SALCARE® SC92 by Ciba-Geigy Corp., High Point, N.C. 27265. POLYQUATERNIUM-32 is particularly preferred.

Still other useful copolymers having a cationic ionic charge are sold under the trademark PERCOL® by Ciba-Geigy Corp., High Point, N.C. 27265 in approximate monomer ratios of about 60/40 to about 40/60 of dimethylaminoethyl acrylate/acrylamide polymer.

Other useful polymeric conditioners include cationic copolymers of methylvinylimadazolium chloride and vinyl pyrrolidone, sold commercially by BASF Aktiengesellschaft, West Germany under the trademark LUVIQUAT® at three comonomer ratios, namely at ratios of 95/5, 50/50 and 30/70 methylvinylimidazolium chloride to polyvinylpyrrolidone. These copolymers at all three comonomer ratios have the CTFA name POLYQUATERNIUM-16.

Other useful polymeric conditioning agents also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named POLYQUATERNIUM-10 in the CTFA Dictionary. Also useful are quaternized copolymers of hydroxyethylcellulose and dimethyldiallylammonium chloride, having the CTFA name POLYQUATERNIUM-4, sold in varying molecular weights under the trademark CELQUAT® by National Starch and Chemical Corporation, Bridgewater, N.J.

It is understood that a number of other polymeric conditioning agents which are commercially available can also be used. The present disclosure of the preferred polymeric conditioning agents is not intended to limit the scope of this invention.

The polymeric quaternary nitrogen-containing conditioning agent can be present at about 0.05 to about 5 weight percent, more preferably at about 0.1 to about 3 weight percent, most preferably at about 0.5 to about 2.0.

The term "relatively viscous" as used herein defines an emulsion based formulation that preferably has a Brookfield viscosity of about 100,000 to greater than about 900,000 centipoises (cps), as measured with a model RVT Helipath spindle No. TE rotating at 5 revolutions per minute (rpm) for one minute at about 25° C.

Useful oleaginous material predominantly include petrolatum, mineral oils and mineral jellies, but can also include lanolin, water-insoluble silicones and like unctuous emulsifiable materials.

Useful petrolatum is available in several grades based upon both viscosity, melting point and color. The Saybolt seconds universal viscosities (S.S.U.) of these products range from between about 50 and about 90 (50/90) S.S.U. at 210° F. (98.9° C.). Preferably, a colorless or "white" product having a Saybolt viscosity of about 55/75 S.S.U. at 210° F. (98.9°.) and melting points in the degree range of 135°/140° F. (59.2°/60° C.) and 127°/137° F. (52.2°/57.8° C.) are used. Preferably, a grade that meets the standards of the United States Pharmacopoeia (U.S.P.) is used.

Mineral oils useful herein are preferably U.S.P. grade white oils. Preferably, a colorless or "white" oil is used having reported typical Saybolt viscosities at 100° F. (37.8° C.) of about 50/350 S.S.U. and specific gravities at 77° F. (24.8° C.) of about 0.822 to about 0.895 (0.822/0.895). The materials having Saybolt viscosities of about 50/60 S.S.U. at 100° F. (37.8° C.) and specific gravities in the ranges 0.822/0.833 at 77° F. (24.8° C.) are preferred. In addition, a mineral jelly compounded of white petrolatum, white mineral oil and wax may also be used as an oleaginous material in the compositions of this invention.

The oleaginous materials may be present in a product emulsion (100 weight percent basis) at about 5 to about 40 weight percent. However, the percentage actually used in a product depends upon the desired product consistency.

For achieving or maintaining phase stability, a lipophilic modified hectorite clay gellant of the type disclosed, for example, in U.S. Pat. Nos. 4,390,033; 4,237,910; 4,524,787; 4,950,485; 5,068,101; 5,171,565 and 5,376,364 optionally can be employed. Phase-stable, relatively viscous creams can be prepared with amounts of up to about 3 weight percent, preferably of up to about 2 weight percent, of these clay gellants based on total weight of cream emulsion component.

Where present, lipophilic hectorite clay gellants are preferably incorporated in pre-gelled form for convenience, as they are known in the art to be difficult to prepare. Pre-gelled oleaginous products containing the above clay gellants are commercially designated by their manufacturer as mastergels.

The mastergels are preferably comprised of hectorite clays modified with (1) a quaternary nitrogen-containing compound such as Stearalkonium chloride or Quaternium-18 which contains at least one $C_8$-$C_{20}$ chain substituent having about 8 to about 20 carbon atoms on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. Stearalkonium chloride and Quaternium-18 are defined in the CTFA Dictionary at pages 704 and 631-632 respectively.

Specific, useful lipophilic hectorite clay gellants which are commercially available as mastergels include: Bentone Gel MIO, comprised of mineral oil, propylene carbonate and QUATERNIUM-18 hectorite; Bentone Gel CAO, comprised of propylene carbonate, castor oil and Stearalkonium hectorite; Bentone Gels SS71 and S130, comprised of mineral spirits (ligroin or petroleum spirits having a boiling range of about 318°-400° F.), propylene carbonate and QUATERNIUM-18 hectorite; and Bentone Gel Lantrol, comprised of propylene carbonate, a mixture of lanolin oil (dewaxed lanolin) and isopropyl palmitate, and Stearalkonium hectorite. The above hectorite clay gellants may be individually used, may be interchanged, one for the other in a given composition, or may be mixed together in a composition.

The foregoing mastergels are commercially available from NL Chemical/NL Industries, Inc., Hightstown, N.J. According to that supplier's product brochures, these mastergels contain about 10 percent modified clay gellant, about 86.7 percent non-polar organic liquid and about 3.3 percent propylene carbonate based on total weight of mastergel as supplied.

Thus, the lipophilic-modified hectorite clay gellant may be present in the cream emulsion component of this invention in amount ranges from zero to up to about 3 weight percent, preferably up to about 2 weight percent, based on total cream emulsion weight.

Useful lipophilic emulsifiers preferably are nonionic emulsifiers which are commercially sold as balanced blends comprising lipophilic fatty alcohols (some distilled or double distilled) derived aliphates from fatty acids containing about 12 to about 24 carbon atoms and adducts thereof with alkylene oxides containing at least two and less than four carbon atoms per starting alkylene oxide. Ethylene oxide adducts are preferred. Particularly preferred are emulsifying waxes containing about 14 to about 20 carbon atoms, more preferably about 16 to about 18 carbon atoms. The term "emulsifying wax" denotes solid nonionic emulsifiers known in the art that are prepared as a mixture of fatty alcohols having from about 12 to about 24 carbon atoms, preferably predominantly lipophilic fatty alcohols having from about 14 to about 20 carbon atoms. Alternatively, the lipophilic nonionic emulsifier can be a balanced blend of the individual lipophilic fatty alcohols, each having about 14 to about 20 carbon atoms, more preferably about 16 to about 18 carbon atoms. Particularly useful fatty alcohols include cetyl alcohol, stearyl alcohol, tallow fatty alcohols and like saturated monovalent linear alcohols obtained from vegetable sources, animal oils and fats and blends thereof.

Preferably, emulsifying waxes meet the standards of the National Formulary (N.F.) or British Pharmacopoeia (B.P.) and can be either the non-self-emulsifying or the self-emulsifying type. Self-emulsifying waxes are typically prepared with an auxiliary hydrophilic nonionic emulsifier present. The hydrophilic nonionic emulsifiers present are usually polyoxyethylene derivatives of fatty acid esters of sorbitol and sorbitol anhydride. Preferred are polysorbates which generally comprise mixtures of oleate or stearate esters condensed with ethylene oxide.

A preferred N.F. grade emulsifying wax is prepared from cetostearyl alcohol containing a polyoxyethylene derivative of a fatty acid ester of sorbitan. This material is known as Emulsifying Wax N.F. and is a creamy white, wax-like solid which is freely soluble in ether, chloroform, alcohol and most hydrocarbon solvents, but is insoluble in water. It melts at a temperature between 48° C. and 52° C., has a hydroxyl value between 178 and 192, an iodine value not more than 3.5, a saponification value not more than 14, and a pH (in a dispersion of 3 parts in 100 parts of water) between 5.5 and 7.0. Emulsifying Wax N.F. is commercially available from a number of suppliers. Exemplary and preferred materials are sold under the name POLAWAX by Croda, Inc., New York, N.Y.; and LIPOWAX P by Lipo Chemicals, Inc., Paterson, N.J.

Particularly preferred are fatty alcohols manufactured and sold under the trademark HYDRENOL D or DD by Henkel KGaA, West Germany. According to the manufacturer, these materials comprise zero-2 percent $C_{12}$; 3-7 percent $C_{14}$; 25-35 $C_{16}$; 60-70 percent $C_{18}$; and zero to 2 percent $C_{20}$ moieties; less than 1.2 percent hydrocarbons, less than 0.3 percent water; and has an acid value of less than 0.1; a saponification value of less than 1.2; an iodine value of less than 1; a hydroxyl value of 210-220; and solidifies in the range of 48'-52° C. Another preferred nonionic emulsifier is a fatty alcohol mixture containing cetyl and stearyl alcohols sold under the trademark TA1618F by The Procter & Gamble Company Industrial Chemicals Divisions, Cincinnati, Ohio.

In the practice of this invention, useful lipophilic nonionic emulsifiers are generally present at about 3 to about 15 weight percent, preferably at about 5 to about 12, more preferably at about 6 to about 10, based on total emulsion weight.

Useful hydrophilic emulsifiers are water-dispersible and water-soluble amphoteric surfactants, zwitterionic surfactants and nonionic surfactants. Anionic surfactants are also useful providing they do not negate the positive charge (cationic properties) of quaternary-nitrogen containing conditioning agents (if present).

A zwitterionic surfactant contains both cationic and anionic moieties in the same molecule, which form inner salts. Amphoteric surfactants that become anionic at alkaline pH and zwitterionic surfactants are preferred.

Useful zwitterionic surfactants include betaines and the related amphoteric sultaines derived from amino propane sulfonic acids. Examples of commercially available betaines include but are not limited to cocamidopropyl betaine, lauramidopropyl betaine, oleamidopropyl betaine, isostearamidopropyl betaine, coco betaine, cetyl betaine, oleyl betaine, coco/oleamidopropyl betaine, tallow or vegetable derived dihydroxyethyl betaine, wheat germamidopropyl betaine and the like. Particularly preferred is cocamidopropylbetaine. Examples of commercially available sultaines include but are not limited to cocamidopropyl hydroxysultaine, lauryl hydroxysultaine and the like.

Suitable amphoteric surfactants include alkylamphocarboxypropionates, and alkylamphoglycinates having mono- or di-carboxyl groups derived from fatty acids having about 10 to about 22 carbon atoms in the fatty alkyl chain. Particularly preferred is stearoamphoglycinate, the CTFA name for 2-heptadecyl-1-carboxymethyl-1-(2-hydroxyethyl)-2-imidazolinium chloride, sold under the trademark Miranol® DM by the Miranol Chemical Company, Inc., South Brunswick (Dayton), N.J. Additional amphoteric surfactants include the class having an aminopropionate structure, such as N-fatty alkyl beta propionic acid and alkali metal salts thereof. Commercial materials having lauryl, myristyl, coco and tallow fatty alkyl groups are sold commercially under the tradename DERIPHAT® by General Mills Chemicals, Inc., Cosmedia Group, Minneapolis, Minn.

Nonionic surfactants include polyoxyethylene derivatives of fatty acid esters of sorbitol and sorbitol anhydride; alkyl polygluccosides available through Cognis, Ambler Pa. 19002; polyethylene glycol esters of fatty acids, polyoxyethylene ethers of fatty alcohols, polyethylene oxide-polypropylene oxide condensates and polyoxyethylene lanolin ethers, and the like. Particularly preferred is the polyethylene glycol derivative of lanolin with an average of 75 moles of ethylene oxide identified by the CTFA name, PEG-75 LANOLIN.

Useful anionic emulsifiers may be illustrated by polyoxyethylene oleyl ether phosphates having about 3 to about 20 oxyethylene groups, sodium lauryl sulfate, and the stearic acid anion and the like. Polyoxyethylene (3) oleyl ether phosphate is particularly preferred.

Hydrophilic emulsifiers can be present at about 0.01 to about 10 weight percent, preferably at about 0.5 to about 5 weight percent, more preferably at about 1 to about 3 weight percent, based on total cream emulsion weight.

Useful aliphatic polyhydroxy compounds are water dispersible and contain about 3 to about 6 carbon atoms and are normally liquid at ambient room conditions, such as propylene glycol, glycerin, butylene glycol, hexylene glycol, sorbitol and the like. Particularly preferred is propylene glycol. The aliphatic polyhydroxy compounds can be present at about 0.1 to about 10 weight percent, preferably at about 1 to about 8 weight percent based on cream emulsion weight.

A conditioning hair straightener formulation may also include known cosmetic adjuvants, such as auxiliary emollients, viscosity modifying agents, perfumes, preservatives, and product colorants in a wide variety of conventional amounts.

Good conditioning was achieved with the conditioning hair straighteners of this invention when BTMS or BTMC were employed and conditioning was augmented by the inclusion of POLYQUATERNIUM-6 without loss of improved skin tolerance benefits. Additionally, no yellowing of natural white "gray" hair was noted.

Emulsion forms of the hair relaxers/hair straighteners of the invention may be prepared by any emulsion forming technique, such as by inversion or non-inversion methods.

For example, inversion emulsification is achieved by separately preparing an oil phase containing the substantially anhydrous lipophilic materials and clay gellant, where present, heating and mixing the foregoing materials at a temperature of about 80° C. and about 85° C. until a substantially homogeneous uniform oil phase results; separately preparing an aqueous (water) phase containing the substantially water-soluble components, except for the alkali metal hydroxide and perfume, where present, similarly heating and mixing the foregoing materials until a substantially homogeneous uniform water phase results.

Subsequently, the oil phase and the water phase are combined while maintaining the foregoing said temperature and mixing until a uniform main emulsion batch is obtained. The main emulsion batch is then cooled to a temperature of about 55° C. to about 65° C. and the alkali metal hydroxide and hair conditioner, where present is added, mixing and maintaining the foregoing temperature until a homogeneous highly alkaline cream emulsion is obtained. The highly alkaline cream emulsion is preferably dearated and then cooled to about ambient room temperature of about 25° C. and any remaining optional ingredients, such as perfume are added and mixed into the highly alkaline cream emulsion. On reaching ambient temperature, the resulting viscous cream emulsion can be homogenized by conventional techniques, such as by versation under vacuum or ultrasonic mixing.

When employing the permanent hair straightening products of this invention in a hair straightening procedure, it is preferable that the person (such as a model) on whose head the compositions are used (the model) not wash her (or his) hair for at least 24 hours prior to the straightener treatment. This preference stems from the scalp protecting effect produced by the model's own sebum secretions. In addition, while washing the hair, slight physical damage can occur to the scalp which can become aggravated by the alkalinity of the hair straightener.

The model's hair can be divided into four sections as delineated by the areas separated when hypothetical lines are drawn from ear-to-ear and from nose-to-backbone. Starting with the rear section, the straightener is applied to the hair with the back or smooth side of a comb (opposite from the teeth). Care is taken to avoid putting the composition on the scalp and about ⅛-¼ inch of the root end (lower component) of the hair shaft. This process takes about 8 to about 9 minutes for treatment of all the model's hair.

Each section of the hair is then physically smoothed with the comb back. At this time in the treatment, the scalp and lower sections of the hair shafts are contacted with the hair straightening product. The smoothing step helps to ensure adequate hair shaft penetration and softening, and also puts tension on the hair to help in straightening the hair. The smoothing step is then repeated to facilitate straightening. The total time for smoothing (both the initial and the repeat steps) normally takes from about 5 to about 10 minutes, depending upon the hair length and thickness. Thus, at the time of the repeat smoothing step, the product is on the head for about 13 to about 18 or even about 20 minutes.

The hair relaxer product is then thoroughly and rapidly removed from the hair by rinsing with water having a temperature of about 37° C. The rinsing step is followed by a shampooing with a non-alkaline shampoo. The shampoo is preferably buffered on the acid side of neutral at about pH 4 to about 6 so that residual alkali left in the hair or on the scalp is neutralized. This shampooing step is usually repeated two to three times.

After shampooing, the hair may be further treated with a conditioner to improve wet combing and hair feel. When the conditioning hair straightening emulsion products of this invention are used, no extra conditioning step is needed. The hair may then be set, styled and dried in a desired coiffure as is known in the art.

The following Examples illustrate the no-mix multimineral hair straightening formulations of this invention with generally preferred ingredients but the Examples are not intended to be limited thereby.

EXAMPLE 1

MULTIMINERAL RELAXER - REGULAR STRENGTH

| CTFA NAME | % w/w |
|---|---|
| Mineral Oil | 16.00 |
| Petrolatum | 19.75 |
| Behentrimonium Methosulfate; Cetearyl Alcohol | 4.00 |
| Cetearyl Alcohol | 5.00 |
| Water | 46.73 |
| Calcium Hydroxide (dry, anhydrous) | 0.30 |
| Cocamidopropyl Betaine | 1.84 |
| PEG-75 Lanolin | 1.50 |
| Polyquaternium-6 | 1.20 |
| Lithium Hydroxide (dry, anhydrous) | 1.282 |
| Sodium Hydroxide (dry, anhydrous) | 0.25 |
| Fragrance | 0.15 |
| Propylene Glycol | 2.00 |
| TOTAL | 100.00 |

The hair relaxer formulation can be made in accordance with the procedures set forth in Example 4.

EXAMPLE 2

MULTIMINERAL RELAXER - SUPER STRENGTH

| CTFA NAME | % w/w |
|---|---|
| Mineral Oil | 16.00 |
| Petrolatum | 19.75 |
| Behentrimonium Methosulfate; Cetearyl Alcohol | 4.00 |
| Cetearyl Alcohol | 5.00 |
| Water | 46.58 |
| Calcium Hydroxide (dry, anhydrous) | 0.30 |
| Cocamidopropyl Betaine | 1.84 |
| PEG-75 Lanolin | 1.50 |
| Polyquaternium-6 | 1.20 |
| Lithium Hydroxide (dry, anhydrous) | 1.43 |
| Sodium Hydroxide (dry, anhydrous) | 0.25 |
| Fragrance | 0.15 |
| Propylene Glycol | 2.00 |
| TOTAL | 100.00 |

The hair relaxer formulation can be made in accordance with the procedures set forth in Example 4.

EXAMPLE 3

Multimineral Relaxer Mild Strength

| CTFA Name | Feature | % W/W |
|---|---|---|
| Water/Aqua | Primary Solvent | 46.97 |
| Calcium Hydroxide | Active | 0.30 |
| Petrolatum | Emollient | 19.75 |
| Mineral Oil | Lubricant | 16.00 |
| Cetearyl Alcohol | Co-Emulsifier | 5.00 |
| Behentrimonium Methosulfate | Co-Emulsifier, Antistatic Agent | 4.00 |
| Cocamidopropyl Betaine | Surfactant | 1.84 |
| PEG-75 Lanolin | Stability enhancer | 1.50 |
| Polyquaternium-6 | Conditioner | 1.25 |
| Lithium Hydroxide | Active | 1.14 |
| Propylene Glycol | Humectant | 2.00 |
| Sodium Hydroxide | Active | 0.25 |
| Total | | 100.00 |

The hair relaxer formulation can be made in accordance with the procedures set forth in Example 4.

EXAMPLE 4

Multimineral Relaxer Super Strength

| Item | CTFA Name | % W/W |
|---|---|---|
| 1 | Water/Aqua | 42.68 |
| 2 | Calcium Hydroxide | 0.30 |
| 3 | Petrolatum | 19.75 |
| 4 | Mineral Oil | 16.00 |
| 5 | Cetearyl Alcohol | 5.00 |
| 6 | Behentrimonium Methosulfate | 4.00 |
| 7 | Cocamidopropyl Betaine | 1.84 |
| 8 | PEG-75 Lanolin | 1.50 |
| 9 | Polyquaterium-6 | 1.25 |
| 10 | Lithium Hydroxide | 1.43 |
| 11 | Propylene Glycol | 2.00 |
| 12 | water* | 4.00 |
| 13 | Sodium Hydroxide | 0.25 |

Procedures:

The identity of the codes in this example are identical to those used in Example 3.

1. Add item #1 to a clean beaker, then add item #2. Mix well and begin to heat between 85-80° C.
2. At 80° C., add items 3-8 in increments of 5-10 minutes between additions. Mix well until completely dissolved.
3. Begin to cool batch. At 60-55° C., add items 9-11 and mix well.
4. Pre-mix items 12 and 13. Check alkalinity, add to batch at 50-45° C.
5. Continue to cool the 25° C. and pass through a colloid mill or versator.

Note that in Examples 1-3 and 5, the water is represented as a single amount. In this example, the amount is broken into two additions to reflect dilution of NaOH in step 4. The amounts reflected in Examples 1-3 and 5 may be split in the same manner.

| | Standard | Example 4 |
|---|---|---|
| Appearance | smooth Crème | Matches Standard |
| Color | white | Matches Standard |
| pH | 12.70-13.20 | 12.9 |
| Viscosity | 25-45 DU | 27.2 |

-continued

| | Standard | Example 4 |
|---|---|---|
| Rheomat 180M Spindle #4 for 60 seconds | | |
| Specific Gravity | 0.94-0.98 | 0.98 |
| Total Alkalinity | 0.75-0.80 | 0.78 |

EXAMPLE 5

MULTIMINERAL RELAXER - KOH SUPER STRENGTH

| CTFA NAME | % w/w |
|---|---|
| Mineral Oil | 16.00 |
| Petrolatum | 19.75 |
| Behentrimonium Methosulfate; Cetearyl Alcohol | 4.00 |
| Cetearyl Alcohol | 5.00 |
| Water | 46.58 |
| Calcium Hydroxide (dry, anhydrous) | 0.30 |
| Cocamidopropyl Betaine | 1.84 |
| PEG-75 Lanolin | 1.50 |
| Polyquaternium-6 | 1.20 |
| Lithium Hydroxide (dry, anhydrous) | 1.43 |
| Potassium Hydroxide (dry, anhydrous) | 0.25 |
| Fragrance | 0.15 |
| Propylene Glycol | 2.00 |
| TOTAL | 100.00 |

The hair relaxer formulation can be made in accordance with the procedures set forth in Example 4.

EXAMPLE 6

Analysis of Relaxers: Diameter Studies and Tensile Properties

Three relaxers were tested on normal brown hair from one individual. The relaxers included three formulas, Precise (Super Strength), Sensitive by Nature (Super Strength), and Multi-Mineral (Super Strength), as produced in Example 2.

| Test | Precise (Super) | SBN (Super) | Multi-Mineral (Super) |
|---|---|---|---|
| % NaOH (50%) | 4.5 | 4.5 | 0.5 |
| % Propylene Glycol | 3 | 2 | 2 |
| % Total Emulsifier | 12.75 | 13.75 | 12.34 |
| % Oil Phase | 36 | 30 | 35.75 |
| Cationic Polymer (40%) | 1.25 | 0 | 1.2 |
| PH | 13.30-13.50 | 13.30-13.50 | 12.70-13.20 |

In each case, the relaxer was carefully worked into the hair to thoroughly saturate the hair swatch. The relaxers were left on the hair for 20 minutes at room temperature. The hair was then rinsed thoroughly with warm water and air-dried. The hair was then crimped for analysis using the Dia-Stron, Miniature Tensile Tester, and Laser Scan Micrometer. The hair was stretched in water, with 75 fibers per relaxer.

The Precise relaxer caused the greatest swelling of the hair in water, as compared to the normal hair. The Sensitive by Nature relaxer had the smallest cross-section area compared to the normal hair. It swelled the least, with statistically significant differences between the values.

The tensile properties of the hair are presented as Load at 15% gram forces or "gmf." Multi-Mineral relaxer produced stronger hair than either Sensitive by Nature or Precise relaxer as compared to normal hair strength at 15%. The values showed statistical significant differences.

The Young's Modulus indicated that Sensitive by Nature relaxer produced stronger hair than Multi-Mineral and Precise. The values showed statistical significant differences.

| Hair Type | Cross-section sq. micron | Load at 15% gmf | Load at break gmf | Young's Modulus MPa |
|---|---|---|---|---|
| Normal | 3082 +/− 827 | 21.6 +/− 2.9 | 73.4 +/− 14.0 | 639.6 +/− 152.5 |
| Sensitive by Nature | 4910 +/− 1300 | 15.5 +/− 3.5 | 64.1 +/− 13.9 | 195.5 +/− 74.2 |
| Multi Mineral | 5540 +/− 1510 | 16.3 +/− 3.4 | 64.2 +/− 13.5 | 171.4 +/− 86.9 |
| Precise | 6210 +/− 1770 | 12.4 +/− 3.8 | 53.6 +/− 12.8 | 98.1 +/− 53.0 |

The relaxer of the present invention provided similar or superior results to prior art hair relaxers containing dramatically higher amounts of sodium hydroxide and considerably higher pH. Indeed, both the Precise Super and the Sensitive by Nature Super relaxers contain pHs which range greater than 13.3, while the Multimineral hair relaxer of the present invention exhibited a pH range from 12.70 to 12.90. As it will be recalled, the pH is a logarithmic scale, these differences in pH are significant.

The multimineral relaxer was tested to confirm that the generally lower pH and sodium hydroxide contents of the products of the invention translated into improved comfort and performance. The evaluations were recorded on questionnaires by in-house hair stylists who tested the relaxer system on the hair of volunteers. Each questionnaire contained information about the client's hair, the processes the stylist used when applying products, the stylist's opinions about the products used and in each of the five steps of the styling process, the client's opinion about the outcome of the relaxer/maintenance system on their own hair. A total of 49 tests were conducted with some of the clients receiving multiple treatments. In terms of handling, 94% of the hair stylists reported that the consistency of the multimineral hair relaxer formulations of the present invention was just right (46 out of 49, with three suggesting that it was too thick). More than ⅔ of the stylists (69.4%) said that the formulations were just right in terms of ease of application. 73.5% of the 49 hair relaxer procedures performed were performed using a regular strength multimineral hair relaxer as described in Example 1. 26.5% (13 applications) used a milder strength. For 62.5% of the clients, the relaxer processing time was 12 to 15 minutes and none of the processing took more than 18 minutes. Rinsing of the relaxer was reported as being either extremely easy 25% of the time or easy 75% of the time.

In terms of comfort, almost all of the clients, 87.2%, said that they were comfortable with no irritation or sensation. Only a few felt some minor irritation (12.8%, 6 of 47 applications—two of the questionnaires were silent on this point). However, for five out of six of the clients who had experienced some irritation, 83.3% of them reported that the level of irritation they experienced was less than that which they experienced from their usual relaxer. After rinsing the relaxer, but before applying any post-relaxer conditioner, the straightness, condition and strong feel of the hair was rated as excellent for the overwhelming majority of the clients (70.9% for straightness; 79.2% for condition; and 81.2% for strong feel, respectively). Thus, with lower sodium hydroxide content, lower overall hydroxide content and lower pH, the use of multimineral hair relaxer was able to achieve comparable if not superior results with the right balance of handling properties and superior comfort and safety for its clients.

What is claimed is:

1. A no-mix hair relaxer formulation comprising: LiOH in an amount of between about 0.74% and about 1.53% by weight of the formulation, NaOH in an amount of between about 0.11% and about 1.23% by weight of the formulation, said hydroxides mixed with at least one cosmetically acceptable additive comprising an emulsifier and $Ca(OH)_2$, said formulation having a pH in a range of greater than 12.7 to about 13.2 and wherein $Ca(OH)_2$ is present in an amount of between about 0.30% and about 0.50% by weight of the formulation.

2. A no-mix hair relaxer formulation comprising:
   LiOH in an amount of between about 0.74% and about 1.53% by weight of the formulation, KOH in an amount which provides an equivalent amount of active hydroxide as would be provided by about 0.11% to about 1.23% of NaOH by weight of the formulation, said hydroxides mixed with at least one cosmetically acceptable additive comprising an emulsifier and Ca(OH)2, said formulation having a pH in a range of greater than 12.7 to about 13.2 and wherein Ca(OH)2 is present in an amount of between about 0.30% and about 0.50% by weight of the formulation.

3. The no-mix hair relaxer formulation of claim 2, wherein said formulation has a pH in a range from greater than 12.7 to about 13.00.

4. The no-mix hair relaxer formulation of claim 1, wherein said LiOH is provided in an amount of between about 0.81% and about 1.53% by weight, and said NaOH is provided in an amount of between about 0.11% and about 1.14% by weight, based on the weight of the total formulation.

5. The no-mix hair relaxer formulation of claim 1, wherein said pH range is from greater than 12.7 to about 13.16.

6. The no-mix hair relaxer formulation of claim 5, wherein said pH range is from greater than 12.7 to about 13.00.

7. A method of straightening hair on the head of a subject comprising the steps of: providing a hair relaxer formulation including LiOH in an amount of between about 0.74% and about 1.53% by weight of the formulation, NaOH in an amount of between about 0.11% and about 1.23% by weight of the formulation, said hydroxides mixed with at least one cosmetically acceptable additive comprising an emulsifier and $Ca(OH)_2$, said formulation having a pH in a range of greater than 12.7 to about 13.2 and wherein $Ca(OH)_2$ is present in an amount of between about 0.30% and about 0.50% by weight of the formulation; and applying said hair relaxer formulation to said subject's hair for a period not to exceed 30 minutes.

8. The no-mix hair relaxer formulation of claim 1, wherein said formulation has a pH in a range of from greater than 12.7 to about 13.16.

9. A method of straightening hair on the head of a subject comprising the steps of: providing a hair relaxer formulation comprising:
   LiOH in an amount of between about 0.74% and about 1.53% by weight of the formulation, KOH in an amount which provides an equivalent amount of active hydroxide as would be provided by about 0.11% to about 1.23% of NaOH by weight of the formulation, said hydroxides mixed with at least one cosmetically acceptable additive comprising an emulsifier and Ca(OH)2, said formulation having a pH in a range of greater than 12.7 to about 13.2 and wherein Ca(OH) 2 is present in an amount of between about 0.30% and about 0.50% by weight of the formulation; and
   applying said hair relaxer formulation to said subject's hair for a period not to exceed 30 minutes.

10. The method of claim 9, wherein said relaxer formulation is in contact with said subject's hair for no more than about 25 minutes.

* * * * *

UNITED STATES PATENT AND TRADEMARK OFFICE
CERTIFICATE OF CORRECTION

PATENT NO. : 7,597,880 B2 Page 1 of 1
APPLICATION NO. : 10/372416
DATED : October 6, 2009
INVENTOR(S) : Darkwa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 933 days.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

PATENT NO.       : 7,597,880 B2
APPLICATION NO.  : 10/372416
DATED            : October 6, 2009
INVENTOR(S)      : Adu Gyamfi Darkwa, Eric Osei-Acquah and Angela D. Ellington It is certified that error appears in the above-identified patent and that said Letters Patent is hereby corrected as shown below:

Column 1, line 56, before "subject" insert --the--.
Column 6, line 2, "suggest" should read --suggests--.
Column 6, line 4, "accomplishes" should read --accomplish--.
Column 6, line 37, after "That is" insert --,--.
Column 7, line 60, "products" should read --product--.
Column 9, line 33, replace "are" with --is--.
Column 9, line 33, "refer" should read --refers--.
Column 11, line 24, replace "has" with --as--.
Column 11, line 33, replace "is" with --are--.
Column 11, line 48, replace "is" with --are--.
Column 12, line 34, "include" should read --includes--.
Column 15, line 49, replace "were" with --was--.
Column 16, line 6, replace "is" with --are--.
Column 20, line 67, replace "was" with --were--.
Column 21, line 26, replace "Ca(OH)2" with --$Ca(OH)_2$--.
Column 21, line 28, replace "Ca(OH)2" with --$Ca(OH)_2$--.
Column 22, line 16, replace "claim 1" with --claim 2--.
Column 22, line 28, replace "Ca(OH)2" with --$Ca(OH)_2$--.
Column 22, line 30, replace "Ca(OH)2" with --$Ca(OH)_2$--.

Signed and Sealed this

Sixteenth Day of November, 2010

David J. Kappos
*Director of the United States Patent and Trademark Office*